United States Patent [19]

Mughal

[11] Patent Number: 4,532,253

[45] Date of Patent: Jul. 30, 1985

[54] OXAPROZIN CALCIUM SALT PHARMACEUTICAL COMPOSITIONS

[75] Inventor: Ahmed S. Mughal, High Wycombe, England

[73] Assignee: John Wyeth & Brother Limited, Maidenhead, England

[21] Appl. No.: 629,704

[22] Filed: Jul. 11, 1984

Related U.S. Application Data

[63] Continuation-in-part of Ser. No. 371,904, Apr. 26, 1982, Pat. No. 4,465,838.

[30] Foreign Application Priority Data

Apr. 28, 1981 [GB] United Kingdom ............... 8113074

[51] Int. Cl.³ .......................................... A61K 31/42
[52] U.S. Cl. ..................................... 514/374; 424/44
[58] Field of Search ................................. 424/272, 44

[56] References Cited

U.S. PATENT DOCUMENTS 3,578,671  5/1971  Brown ............................... 424/272

FOREIGN PATENT DOCUMENTS 1206403  9/1970  United Kingdom ............... 424/272

Primary Examiner—Donald G. Daus
Assistant Examiner—S. A. Gibson
Attorney, Agent, or Firm—George Tarnowski

[57] ABSTRACT

The invention concerns pharmaceutical compositions containing a novel oxazole derivative, calcium oxaprozin. The formulations may be for oral or other use. The oral formulations are more palatable than those containing oxaprozin itself.

16 Claims, No Drawings

OXAPROZIN CALCIUM SALT PHARMACEUTICAL COMPOSITIONS

This application is a continuation in part of my co-pending application Ser. No. 371,904 filed Apr. 26, 1982, now U.S. Pat. No. 4,465,838.

This invention relates to pharmaceutical compositions containing a novel oxazole derivative.

Oxaprozin, namely $\beta$-(4,5-diphenyloxazol-2-yl) propionic acid has shown interesting anti-inflammatory activity and is currently undergoing clinical trials in humans as an anti-inflammatory agent.

Unfortunately oxaprozin has a very bitter taste. This can be masked in use by making the dosage forms as capsules or film coated tablets. However, where large single doses of oxaprozin are required this solution to the problem is not satisfactory. Research has been carried out to devise pharmaceutical preparations which allow for once a day dosing. Such preparations include chewable tablets containing a relatively large amount of oxaprozin and suspensions. The bitter taste of oxaprozin has proved to be a disadvantage of such preparations.

In our researches we have prepared various salts of oxaprozin and have found that the calcium salt does not possess the bitterness of the parent acid. On the other hand the sodium salt of oxaprozin is quite bitter.

The present invention therefore provides pharmaceutical formulations containing the calcium salt of $\beta$-(4,5-diphenyloxazol-2-yl)propionic acid.

The calcium oxaprozin may be prepared by treating oxaprozin with a source of calcium ions. Preferably a water soluble salt of oxaprozin is treated with a source of calcium ions. The water soluble salt may be an alkalimetal salt e.g. the sodium or potassium salt, an ammonium salt, or an amine salt. Preferably the water soluble salt of oxaprozin is reacted with a water soluble calcium salt e.g. calcium chloride, calcium nitrate, calcium acetate, or calcium formate in aqueous solution. The resulting calcium oxaprozin is precipitated. In some circumstances it may be obtained as the tetrahydrate.

Although the calcium oxaprozin has been developed primarily for palatable oral pharmaceutical preparations it may be used in other formulations e.g. suppositories or pessaries.

The pharmaceutical formulations include solids and liquids. Any suitable carrier known in the art can be used to prepare the pharmaceutical composition. In such a composition, the carrier is generally a solid or liquid, or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aids, binders, effervescent excipients or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 10 to 80%, preferably 25 to 75% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, suspensions, emulsions, syrups and elixirs. The active ingredient, for example, can be suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil).

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders. The unit dosage form can be, for example, a capsule or tablet itself, or it can be the appropriate number of any such compositions in package form. The quantity of the active ingredient in a unit dose of composition may be varied or adjusted from 100 mg or less to 800 mg or more, according to the particular need. Preferably calcium oxaprozin is present in an amount from 200 to 750 mg, preferably from 400 to 750 mg.

The invention also provides a chewable tablet comprising calcium oxaprozin, a chewable base, a binding agent and a lubricant. The tablet may include finely divided silica, sweetening agents and flavouring agents. The chewable base is preferably mannitol. Other chewable bases which may be used are sorbitol or directly compressible sucrose.

A chewable tablet according to the invention comprises:

| | |
|---|---|
| Calcium oxaprozin | 600–800 mg |
| Chewable base | 300–600 mg |
| a binding agent, a sweetening agent and a lubricant. | |

A preferred chewable tablet comprises:

| | |
|---|---|
| Calcium oxaprozin | 600–800 mg |
| Mannitol | 300–600 mg |
| binding agent | up to 300 mg |
| lubricant | |
| sweetening agent | |
| flavouring agent | |

The binding agent preferably comprises one or more of the following polyvinyl pyrrolidone, starch, or cellulose binding agents e.g. methylcellulose, hydroxypropyl methyl cellulose, hydroxypropyl cellulose and microcrystalline cellulose.

One particular chewable tablet according to the invention may comprise:

| | |
|---|---|
| Calcium oxaprozin | 600–800 mg |
| Mannitol | 300–600 mg |
| Polyvinyl pyrrolidone | 30–70 mg |
| Starch | 100–300 mg |
| finely divided silica | up to 40 mg |
| magnesium stearate | up to 50 mg |
| sweetening agent and flavouring agent. | |

In the above formulation the polyvinyl pyrrolidone may be replaced by methyl cellulose.

A suspension according to the invention comprises calcium oxaprozin, wetting agents, preserving agents, suspending agents, sweeteners and water. Flavouring agents may be added. The amount of calcium oxaprozin may be in the range from 0.75–2.0 g per 5 ml of suspension.

Preferred wetting agents are polyoxyethylene surface active agents of the Tween type, (Tween is a registered Trade Mark), such as polysorbate 80 (Tween 80). Other wetting agents such as glycerol may be used.

A preferred suspension comprises calcium oxaprozin 0.75–2.0 g per 5 ml, polysorbate 80 and glycerol.

The dosage forms of the present invention may be made into effervescent tablets comprising calcium oxaprozin, an effervescing agent, binding agent, and a lubricant. The effervescing agent may comprise sodium glycine carbonate and/or sodium bicarbonate.

Another specific dosage form according to the invention is an effervescent tablet comprising:

| | |
|---|---|
| Calcium oxaprozin | 600–800 mg |
| Mannitol or sucrose | 300–600 mg |
| Sodium glycine carbonate | 100–200 mg |
| Sodium bicarbonate | 100–200 mg |
| Citric acid | 300–400 mg |
| Binding agent | 50–150 mg |
| finely divided silica | up to 40 mg |
| lubricant s.g. dl leucine or magnesium stearate | up to 100 mg |
| sweeteners and flavouring agents | |

The invention is illustrated by the following examples:

EXAMPLE 1

β-(4,5-Diphenyloxazol-2-yl)propionic acid calcium salt

β-(4,5-Diphenyloxazol-2-yl)propionic acid (oxaprozin) was converted to the sodium salt by stirring the acid (6 kg) in distilled water (60 kg) and 46–48% sodium hydroxide liquor (1.85 kg). A filtered solution of calcium chloride dihydrate B.P, (2.44 kg) in distilled water was added and the title compound precipitated as a white solid. This was collected on a vacuum filter and washed with distilled water until the filtrate was free from chloride. The product was dried in an air oven to give a yield of 6.7 kg (98% of theory) of the title compound as a tetrahydrate.

Found: C, 61.48; H, 5.02; N, 3.67% $(C_{18}H_{14}NO_3)_2Ca.4H_2O$ requires: C, 62.0; H, 5.17,; N, 4.02%. Calcium content was determined by Gravimetric analysis to be 6.4% (Theoretical 5.75%).

EXAMPLE 2

Chewable Tablet

The calcium salt of Example 1 was formulated into chewable tablets of the following composition per tablet

| | mg per tablet |
|---|---|
| Calcium oxaprozin | 712.5* |
| Mannitol | 500 |
| Polyvinyl pyrrolidone | 46.6 |
| Water | q.s. |
| StaRx 1500 starch | 212.0 |
| Saccharin sodium | 1.5 |
| Liquorice | 2.20 |
| Aniseed | 2.20 |
| Aerosil 200 (finely divided silica) | 8.00 |
| Magnesium stearate | 38.0 |
| | 1523 |

*Equivalant to 600 mg oxaprozin.

The tablets were prepared by the following procedure. The polyvinyl pyrrolidone was dissolved in sufficient water and the calcium oxaprozin granulated with it. Mannitol previously passed through a 30 mesh screen was added. The wet granules were dried and graded to 12 mesh screen at 50° C. The dried granules were passed through 16 mesh screen. The liquorice and aniseed were dispersed onto some StaRx 1500. The rest of the ingredients were weighed out and blended with the dried granules and the flavoured StaRx 1500.

The tablets were compressed on a standard tabletting machine to form chewable tablets. The tablets were found to be quite palatable in contrast to similar tablets of oxaprozin which were so bitter as to be unpalatable.

EXAMPLE 3

A suspension of calcium oxaprozin (from Example 1) was prepared to have the following ingredients per 100 ml.

| | % w/v |
|---|---|
| Calcium Oxaprozin | 14.25 |
| *Glycerin | 40.00 |
| Avicel CL 611 (microcrystalline cellulose) | 1.20 |
| **Grapefruit flavour - Givauden 73836 | 0.10 |
| ***Nipagin M (sodium methyl para hydroxy benzoate) | 0.04 |
| ***Nipagin A (sodium ethyl para hydroxy benzoate) | 0.06 |
| ***Nipasol M (sodium propyl para hydroxy benzoate) | 0.10 |
| Purified water to | 100 ml |

*Level may vary - 40–50% w/v, water content being adjusted accordingly.
**May be substituted by other suitable flavours.
***Preservative levels may be changed, Nipasol M may be omitted.

A suitable colour may be added. Glycerine functions as wetting agent and sweetener.

Method of Manufacture

The Avicel is dispersed in approximately 90% of the water. The glycerin is added to the dispersion and mixed in. The calcium oxaprozin is added to the glycerin/Avicel mixture and dispersed. The preservatives are then added and the suspension as a 40% concentrate in water. Finally the flavour is added and mixed in.

EXAMPLE 4

Effervescent Tablet

An effervescent tablet was made up according to the following formulation:

|  | mg/tablet |
| --- | --- |
| Calcium oxaprozin | 712.50 |
| Polyvinyl pyrrolidone | 100.00 |
| Sodium glycine carbonate | 150.00 |
| Sodium bicarbonate | 150.00 |
| Mannitol | 429.50 |
| *IMS OP 74 qs | |
| Citric acid anhydrous | 350.00 |
| Sodium saccharin | 4.00 |
| Lemon 842601/B | 4.00 |
| dl Leucine | 100.00 |
| | 2000.00 |

*Industrial Methylated Spirits (99.5% Ethyl Alcohol)

Process of Preparation

Weigh out and sieve through a No. 30 screen calcium oxaprozin, sodium glycine carbonate, sodium bicarbonate and mannitol. Granulate with an IMS solution of PVP. Pass the wet mass through a No. 12 screen, and after drying through a No. 16 screen. Blend the dried granule with citric acid anhydrous, sodium saccharin, flavour and leucine in a humidity controlled area. Compress into tablets using 19 mm tooling and assemble into a pack which excludes moisture.

EXAMPLE 5

Chewable Tablet

Chewable tablets were made up according to the following formulation:

|  | mg per tablet |
| --- | --- |
| Calcium oxaprozin | 712.5* |
| Mannitol | 500.0 |
| **Methocel A15 | 45.0 |
| Water qs | |
| Starch 1500 | 212.1 |
| Saccharin sodium | 1.5 |
| Liquorice | 2.2 |
| Aniseed | 2.2 |
| Aerosol 200 (finely divided silica) | 22.5 |
| Magnesium Stearate | 15.0 |
| | 1513.0 |

* Equivalent to 600 mg Oxaprozin
** Methyl Cellulose

Process of Preparation

Dissolve Methocel A15 in deionized water and leave overnight at 4° C. Mix calcium oxaprozin in a planetary mixer with mannitol and granulate with Methocel aqueous solution. Blend the remaining excipients in a suitable planetary mixer. Compress on a suitable compression machine fitted with 19 mm punches.

EXAMPLE 6

Chewable tablets are made up according to the following formulation using the procedure described in Example 5

|  | mg per tablet |
| --- | --- |
| Calcium oxaprozin | 712.5 |
| Mannitol | 500.0 |
| Methocel A15 premium | 45.0 |
| Water | q.s. |
| Microcrystalline cellulose | 212.1 |
| Saccharin | 1.5 |
| Liquorice | 2.2 |

|  | mg per tablet |
| --- | --- |
| Aniseed | 2.2 |
| Aerosol 200 | 22.5 |
| Magnesium stearate | 15.0 |
| | 1513.0 |

EXAMPLE 7

Effervescent Tablet

|  | mg per tablet |
| --- | --- |
| (A) Wet granulation | |
| Calcium oxaprozin | 712.5* |
| **Dipak | 200.0 |
| Sodium glycine carbonate | 150.0 |
| Hydroxy propyl cellulose | 100.0 |
| IMS (Industrial Methylated Spirit) | q.s. |
| (B) Powder blending mixture | |
| Dipak | 199.1 |
| Sodium bicarbonate coated | 150.0 |
| Citric acid coated | 350.0 |
| Liquorice | 2.2 |
| Aniseed | 2.2 |
| Aerosol 200 | 10.0 |
| Sodium saccharin | 4.0 |
| Magnesium stearate | 20.0 |
| | 1900.0 |

*Equivalant to 600 mg oxaprozin
**Directly compressible sucrose

Weigh out calcium oxaprozin, dipak, sodium glycine carbonate and mix in a planetary blender. Dissolve hydroxypropyl cellulose in IMS and granulate the powder blend. Pass the mass through 12 mesh screen and dry. Pass the dried granules through 16 mesh screen, blend in the remaining excipients in planetary mixer, compress on a suitable compression machine fitted with 19 mm FBE punches.

All mesh sizes in the above examples are British Standard sizes: 12 mesh=1400 microns, 16 mesh=1000 microns, 30 mesh=500 microns.

EXAMPLE 8

Chewable Tablet

| Ingredients | mg/tablet |
| --- | --- |
| Calcium Oxaprozin | 712.50 |
| Mannitol | 350.00 |
| Microtal Sugar (Directly Compressible sucrose)(TATE & LYLE) | 150.00 |
| Avicel PH 101 (Micro crystalline cellulose) | 83.05 |
| Talin*(TATE & LYLE) | 0.05 |
| Methocel A15 Premium | 75.00 |
| Water q.s. | |
| Microtal Sugar | 50.00 |
| Liquorice GB 1786 ex H&R | 2.20 |
| Aniseed GB 1784 ex H&R | 2.20 |
| Magnesium Stearate BP | 45.00 |
| Aerosol 200 | 30.00 |
| | 1500.00 |

*Naturally occurring sweet proteins - THAUMATIN I & II mol. wgt. $T_1$ = 22,209 and $T_2$ = 21,000 ± 500.
BRITISH APPROVED NAME - THAUMATIN - TRADE NAME TALIN (TATE & LYLE).
(microcrystalline cellulose) and granulate with Methocel

Process of Preparation

Dissolve Methocel A15 in deionised water and leave overnight at 4° C. Mix calcium oxaprozin in a planetary mixer with mannitol, Microtal sugar and Avicel PH 101 (microcrystalline cellulose) and granulate with Methocel aqueous solution. Blend the remaining excipients in a suitable planetary mixer. Compress on a suitable compression machine fitted with 19 mm punches.

Suppository Formulation

Method 1

Suppositories containing calcium oxaprozin may be prepared by standard methods by dispersing calcium oxaprozin in Witepsol H-32 (a semi-synthetic triglyceride manufactured by Dynamit Nobel) to produce suppositories containing 712.50 mg calcium oxaprozin each or containing 1425 mg calcium oxaprozin each.

Method 2

The Witepsol H-32 of method 1 may be replaced by cocoa butter.

I claim:

1. A pharmaceutical formulation comprising as active ingredient calcium oxaprozin and a pharmaceutically acceptable carrier.

2. A pharmaceutical formulation as claimed in claim 1, in unit dosage form, wherein the amount of calcium oxaprozin present ranges from 100 to 800 mg per unit dose.

3. A pharmaceutical formulation as claimed in claim 2, in the form of a chewable tablet comprising calcium oxaprozin, chewable base, binding agent and lubricant.

4. A pharmaceutical formulation as claimed in claim 3, wherein the chewable base is mannitol, directly compressible sucrose or sorbitol.

5. A pharmaceutical formulation as claimed in claim 2, in the form of an effervescent tablet comprising calcium oxaprozin, effervescing agent, binding agent and a lubricant.

6. A pharmaceutical formulation as claimed in claim 2, wherein finely divided silica is incorporated in the mixture.

7. A pharmaceutical formulation as claimed in claim 2, wherein the binding agent is selected from polyvinyl pyrrolidone, starch and cellulosic binding agents e.g. methylcellulose, hydroxypropyl methylcellulose, hydroxypropyl methylcellulose, hydroxypropyl cellulose and microcrystalline cellulose.

8. A pharmaceutical formulation as claimed in claim 2, in the form of a chewable tablet comprising calcium oxaprozin 600–800 mg, chewable base, 300–600 mg, up to 300 mg of binding agent, a sweetening agent and a lubricant.

9. A chewable tablet comprising:
Calcium oxaprozin: 600–800 mg
Mannitol: 300–600 mg
Polyvinyl pyrrolidone: 30–70 mg
Starch: 100–300 mg
finely divided silica: up to 40 mg
magnesium stearate: up to 50 mg
sweetening agent and flavouring agent 10. A chewable tablet comprising:
Calcium oxaprozin: 600–800 mg
Mannitol: 300–600 mg
Methyl cellulose: 30–70 mg
Starch: 100–300 mg
finely divided silica: up to 40 mg
magnesium stearate: up to 50 mg
sweetening and flavouring agents 11. A chewable tablet comprising:
Calcium oxaprozin: 600–800 mg
Mannitol: 300–600 mg
Microcrystalline celluloae: 70–100 mg
Methyl cellulose: 50–100 mg
Magnesium stearate: 40–50 mg
finely divided silica: 20–40 mg
sweetening and flavouring agents 12. A pharmaceutical formulation in the form of a suspension for oral administration comprising calcium oxaprozin, wetting agent, preserving agent, suspending agent, sweetener and water.

13. A pharmaceutical suspension formulation as claimed in claim 12, wherein the calcium oxaprozin is present in the range from 0.50 to 2.0 g per 5 ml of suspension.

14. An effervescent tablet comprising:
Calcium oxaprozin: 600–800 mg
Mannitol or sucrose: 400–600 mg
Sodium glycine carbonate: 100–200 mg
Sodium bicarbonate: 100–200 mg
Citric acid: 300–400 mg
binding agent: 50–150 mg
finely divided silica: up to 40 mg
lubricant: up to 100 mg
sweetener and flavouring agent 15. An effervescent tablet as claimed in claim 14, wherein the lubricant is dl leucine or magnesium stearate.

16. A method of treating inflammation in a mammal in need of such treatment which method comprises administering to said mammal an effective amount of calcium oxaprozin.

* * * * *